(12) United States Patent
Schneider

(10) Patent No.: US 6,196,049 B1
(45) Date of Patent: Mar. 6, 2001

(54) SENSING ELEMENT AND METHOD FOR MANUFACTURING A SENSING ELEMENT

(75) Inventor: Gerhard Schneider, Pettstadt (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/195,943

(22) Filed: Nov. 19, 1998

(30) Foreign Application Priority Data

Nov. 19, 1997 (DE) .............................. 197 51 128

(51) Int. Cl.$^7$ ............................ G01N 19/10; G01N 27/26

(52) U.S. Cl. .............................................. 73/23.2; 204/425

(58) Field of Search ................................ 73/23.2, 31.05; 204/425, 412

(56) References Cited

U.S. PATENT DOCUMENTS

| 4,282,080 | * | 8/1981 | Muller et al. | 204/412 |
| 4,300,990 | * | 11/1981 | Maurer | 204/412 |
| 4,334,974 | * | 6/1982 | Muller et al. | 204/425 |
| 4,505,807 | * | 3/1985 | Yamada | 204/425 |
| 4,610,741 | * | 9/1986 | Mase et al. | 156/89.15 |

\* cited by examiner

*Primary Examiner*—Hezron Williams
*Assistant Examiner*—Jay Politzer
(74) *Attorney, Agent, or Firm*—Kenyon & Kenyon

(57) ABSTRACT

A sensing element, in particular for an electrochemical sensor, for determining the oxygen content of gases, includes at least one first electrode exposed to a measured gas and at least one second electrode exposed to a reference gas. A presintered support receiving a sensing device is provided, a porous adhesion layer, also presintered, being arranged between the support and the sensing device.

8 Claims, 3 Drawing Sheets

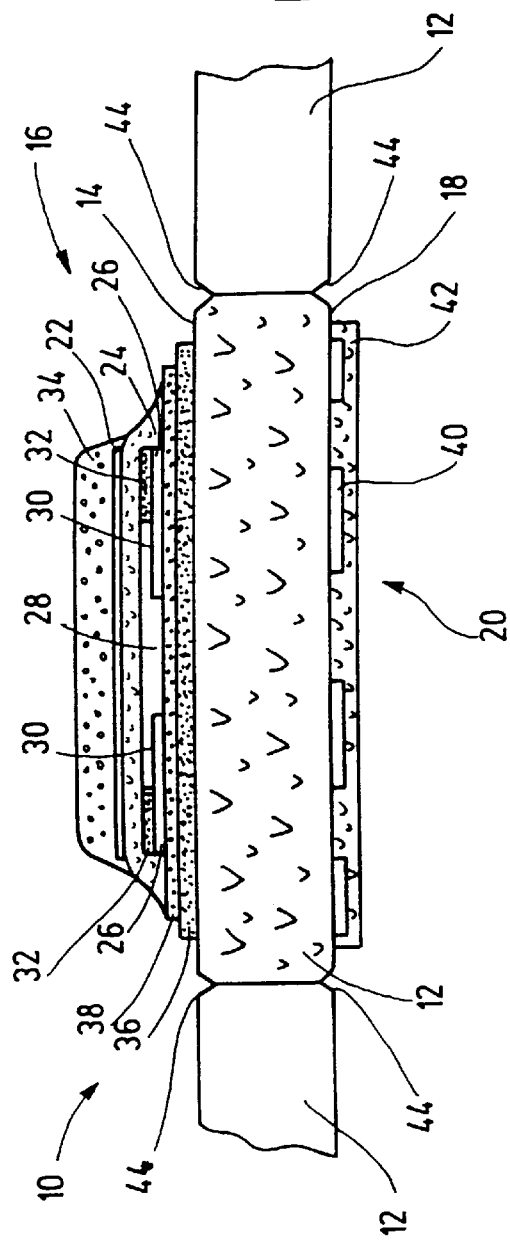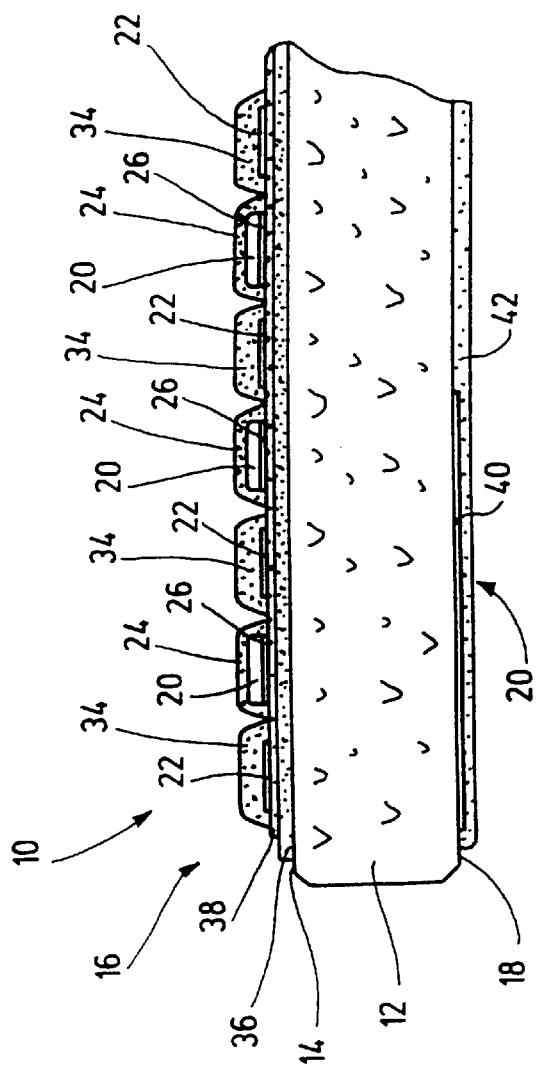

SENSING ELEMENT AND METHOD FOR MANUFACTURING A SENSING ELEMENT

FIELD OF THE INVENTION

The present invention relates to a sensing element, in particular for an electrochemical sensor, for determining the oxygen content of gases, as well as to a method for manufacturing the sensing element.

BACKGROUND INFORMATION

Sensing elements are known. They are configured, for example, as so-called planar sensing elements, which have a first electrode exposed to a measured gas, on a solid electrolyte configured as a support, and a second electrode exposed to a reference gas. In a number of applications, the sensing element must be heated to a specific temperature. It is known for this purpose to associate with the sensing element a heating device, which usually has heating conductors running below the electrode that is exposed to the reference gas.

In order to deliver a reference gas onto the reference gas electrode, a reference gas conduit which extends in the longitudinal direction of the sensing element is provided inside the layered, planar sensing element.

To manufacture sensing elements of this kind, it is known that the individual functional layers yielding the sensing element are arranged one above another as so-called green films, the individual functional layers having a specific layout corresponding to the structure of the sensing element. The entire sensing element is then sintered. It is disadvantageous in this context that, because the functional layers are present as green films, the sensing element is relatively labile; handling both during application of the functional layers and during sintering can thus be performed only with the greatest of care in order to prevent damage to the sensing element.

SUMMARY OF THE INVENTION

The sensing element according to the present invention offers, in contrast, the advantage that the manufacture and handling thereof are simplified. Because the sensing element is patterned on a presintered support, a porous adhesion layer being arranged between the support and the sensing element, a relatively solid support, which is easy to handle and at the same time protects the applied functional layers of the sensing element from mechanical damage, is available both while the individual functional layers of the sensing element are being printed on, and during subsequent sintering of the functional layers.

In a preferred embodiment of the present invention, provision is made for the support to have on its one side a sensing device and on its other side a heating device. It thereby becomes advantageously possible to decouple the manufacture of the heating device from the manufacture of the sensing device, so that they can be accomplished in separate process sequences. In addition to the resulting optimization of both the application of the heating device and the application of the sensing device onto the opposite sides of the support, an increase in yield can also be attained, since when the heating device and the sensing device are manufactured in succession, any heating devices that may be manufactured defectively no longer need to be equipped with the sensing device. This allows not only material but also time and cost to be saved when manufacturing the sensing elements.

In addition, the method according to the present invention for manufacturing the sensing element offers the advantage that the time for sintering the sensing element can be reduced. Because the support substrate is already presintered, all that is necessary is a post-sintering of the applied functional layers. Since the latter are relatively thin, the sintering time can be kept correspondingly short.

BRIEF DESCRIPTION OF THE DRAWINGS

FIG. 1 shows a sectioned depiction through a sensing element in a first exemplary embodiment of the present invention.

FIG. 3 shows a sectioned depiction through a sensing element in a second exemplary embodiment of the present invention.

DETAILED DESCRIPTION

Figure 2:
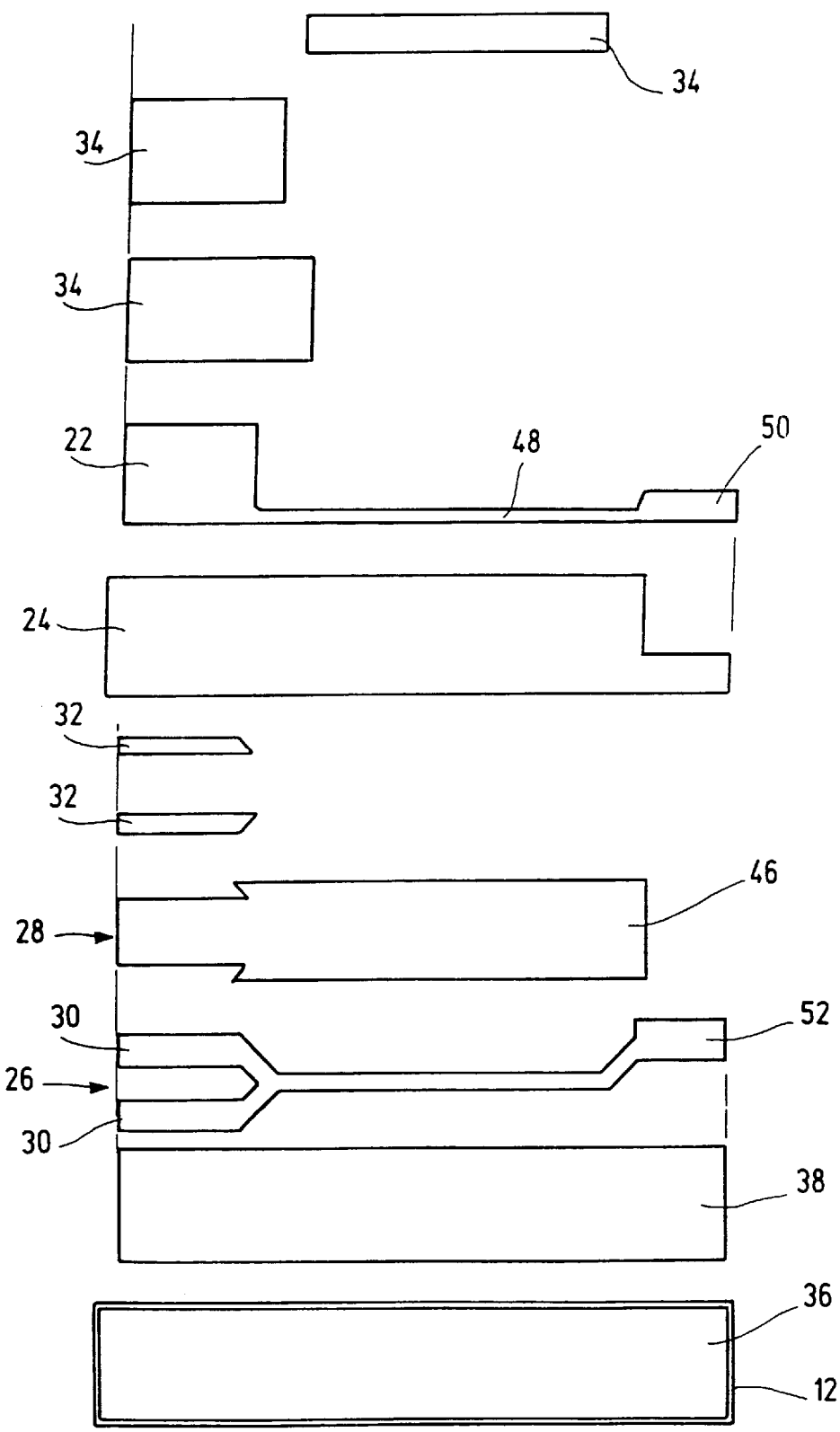
FIG. 2 shows schematic views of the individual functional layers of the sensing element according to FIG. 1.

FIG. 1 shows a sectioned depiction of a sensing element 10. Sensing element 10 includes a support 12 which has on its one side 14—in this case on top—a sensing device 16, and on its other side 18 a heating device 20.

Sensing element 10 possesses a planar layered structure which extends from a measured-gas-side section shown in FIG. 1 to a reference-gas-side section (not depicted) remote from the measured gas. Sensing element 10 is a constituent of an electrochemical sensor (not depicted), and is secured (sealed) in a housing of the sensor. The sensor is exposed to a gas to be measured, for example to the exhaust gas of a motor vehicle. The structure and function of electrochemical sensors which use a Nernst element to analyze a partial pressure difference between a reference gas and a gas to be measured, and make available a corresponding signal, are known.

Sensing device 16 possesses a first electrode 22 which can be exposed to the measured gas, for example to the exhaust gas of a motor vehicle. Electrode 22 is arranged on a solid electrolyte 24 on whose side facing away from electrode 22 a second electrode 26 is arranged. Electrode 26 can be exposed to a reference gas, for example to atmospheric oxygen. A reference gas conduit 28, which extends in the longitudinal direction of sensing element 10 and terminates at the section of sensing element 10 remote from the measured gas, is configured in order to deliver the reference gas. Electrode 26 is of split configuration on the measured-gas-side section, so that it extends out into two arms 30. Arms 30 are partially covered by ion conductors 32 which are arranged in columnar fashion between electrode 26 and the solid electrolyte. Electrode 22 is surrounded by a protective layer 34 which has a minimum porosity allowing a measured gas to come into contact with electrode 22. A partial pressure difference that is established between electrodes 22 and 26 results, via ion conductors 32 and solid electrolyte 24, in an exchange of charge carriers which results in the pickoff of a signal at electrodes 22 and 26, at their connecting contacts (not depicted in FIG. 1) remote from the measured gas.

A porous adhesion layer 36 and a gas-tight base layer 38 are arranged between carrier 12 and sensing device 16.

Heating device 20 has a heating conductor 40, arranged for example in meander fashion, which is covered over by an impervious heater cover layer 42.

According to one exemplary embodiment, support 12 includes an aluminum oxide ($Al_2O_3$)/$ZrO_2$ substrate, adhesion layer 36 of a porous aluminum oxide ($Al_2O_3$) layer, base layer 38 of an yttrium-stabilized zirconium layer ($ZrO_2$/$Y_2O_3$), solid electrolyte 24 of stabilized zirconium oxide, and ion conductors 32 and protective layer 34 of porous zirconium oxide. Electrodes 22 and 26 include, for example, platinum-cermet conductor paths.

Heating conductor 40 also is composed, for example, of a platinum conductor path, while cover layer 42 is composed of an impervious aluminum oxide ($Al_2O_3$).

The manufacture of sensing element 10 shown in FIG. 1 will now be discussed with reference to FIG. 2.

At the outset, support 12 is available as an already sintered aluminum oxide substrate. Support 12 is equipped at least on its side 14, optionally also on side 18, with an adhesion layer 36 that is also already pre-sintered. Support 12 thus forms a relatively stable substrate for the subsequent patterning of sensing device 16.

Provision is preferably made, if sensing element 10 is to have a heating device 20, for heating device 20 to have been applied prior to the patterning of sensing device 16. For this, heating conductor 40 and cover layer 42 are printed onto side 18 of support 12 in successive printing steps, and co-fired together with side 18. The result of this is that the manufacture of heating device 20 is completely decoupled from the manufacture of sensing device 16. The process steps for the manufacture of heating device 20 can thus be performed independently of any process steps for the manufacture of sensing device 16 that may occur later, and can be optimized without consideration of those process steps.

There are thus two ways of arriving at a pre-sintered support 12. According to the first variant, a film yielding support 12 is equipped with the porous adhesion layer 36, and the film is sintered together with adhesion layer 36 at approximately 1600° C. The second possibility is to equip the film yielding support 12 with the porous adhesion layer 36 and with heating conductors 40 and cover layer 42, and to sinter this composite at approximately 1600° C., thus making available for the further preparation of sensing device 16 a pre-sintered support 12 having an already patterned and co-sintered heating device 20.

As FIG. 1 elucidates, the manufacture of sensing elements 10 can take place in a so-called multiple panel; i.e., in parallel process steps, a plurality of sensor elements 10 are produced simultaneously as a result of the successive patterning of the individual functional layers, the individual sensing elements 10 being achieved by subsequent isolation. FIG. 1 indicates that a plurality of sensing elements 10 are simultaneously patterned, next to one another or in front of and/or behind one another, in a specific grid spacing as viewed from above. Isolation can be accomplished, for example, by breaking the substrate of support 12 at indicated break edges 44, which preferably are produced as support 12 is being patterned.

Because the production of heating device 20 is decoupled in process-engineering terms from that of sensing device 16, heating device 20 can very advantageously first be tested, so that, for example on supports 12 having a defective heating device 20, patterning of a sensing device 16 on side 14 opposite heating device 20 can be omitted. This makes it possible to achieve an increase in the yield of the materials used to produce the individual functional layers, since a sensing device 16 is no longer applied onto sensing elements 10 that have already been recognized as defective. In the case of manufacture in a multiple panel, corresponding recognition and microprocessor-controlled patterning of sensing elements 10 can be used to remove support 12 having the defective heating device 20 from the process of patterning sensing device 16. According to further exemplary embodiments, of course, it is possible first to pattern sensing device 16, and then to pattern heating device 20 on the opposite side 18. Here again, analogously, patterning of a heating device 20 on a support having a defective sensing device 16 can be dispensed with. Increased yields of the materials used are obtained in this case as well. For the case in which support 12 is first equipped with sensing device 16, a film of highly sinterable aluminum oxide ($Al_2O_3$), which for example sinters in impervious fashion at a sintering temperature of approximately 1400° C., can be used as the starting material for support 12. For this purpose, this highly sinterable aluminum oxide is equipped with the individual layers yielding sensing device 16, then sintered at approximately 1400° C., and subsequently heating device 20 is once again produced.

In the patterning of sensing device 16, base layer 38 is first printed, for example by screen printing, onto the pre-sintered composite of support 12 with the porous adhesion layer 36 and optionally with heating device 20, and is then pressed into the pre-sintered porous adhesion layer 36. This results in an intimate bond between support 12 and sensing device 16 which persists even during later use of sensing element 10 as intended. In successive printing steps, second electrode 26 is then first printed on, forming its arms 30, followed by a sacrificial layer 46 yielding reference gas conduit 28. Then ion conductors 32, solid electrolyte 24, first electrode 22, and protective layer 34 are printed on. Protective layer 34 is printed on in sub-steps, so that on the one hand the actual electrode 22, and also a conductive path 48 which connects to a connecting contact 50, remote from the measured gas, of electrode 22, are covered.

The schematic plan view of the individual layers shown in FIG. 2 depicts the measured-gas-side section of a sensing element 10 on the left, and its section remote from the measured gas on the right. The layout of the individual functional layers is such that the structure shown in section in FIG. 1 is created in the measured-gas-side section of sensing element 10, while in the section remote from the measured gas, connecting contacts 50 of electrode 22 and 52 of electrode 26 are exposed for making contact with an analysis circuit (not depicted). The thicknesses of the individual functional layers, in particular of solid electrolyte 24 and protective layer 34, are designed to be such that lateral envelopment of electrodes 22 and 26 occurs, i.e. that their outer end surfaces extending in the longitudinal direction of sensor element 10 are covered over.

After application of the functional layers of sensing device 16 onto support 12, the entire sensing element 10 is sintered, support 12 and adhesion layer 36, as well as optionally heating device 20, already being pre-sintered. Sintering is accomplished at a temperature of, for example, 1300 to 1500° C. Once sintering has occurred, sensing elements 10 are isolated from the overall multiple panel by isolating supports 12 at break edges 44 by applying a small force. During sintering, sacrificial layer 46 yielding reference gas conduit 28 is completely dissolved away. This layer can be composed, for example, of carbon, carbon black, theobromine, or other suitable materials.

Because sensing devices 16 are patterned onto an already pre-sintered support 12, handling of the entire multiple panel is on the one hand simplified, since the inherently relatively stable support 12 is available for holding and/or transportation. In addition, sintering can be accomplished in a relatively short time period, since support 12 is already sintered, and a correspondingly shorter time suffices for complete sintering of the functional layers of sensing device 16. As compared with known manufacturing methods, only proven and easily controllable process steps, such as printing, pressing, and sintering, are necessary. Any punching operations, through-plating, or cutting operations in order to isolate sensing elements 10, which are relatively incompatible with the manufacturing methods used, can be dispensed with.

Figure 4:
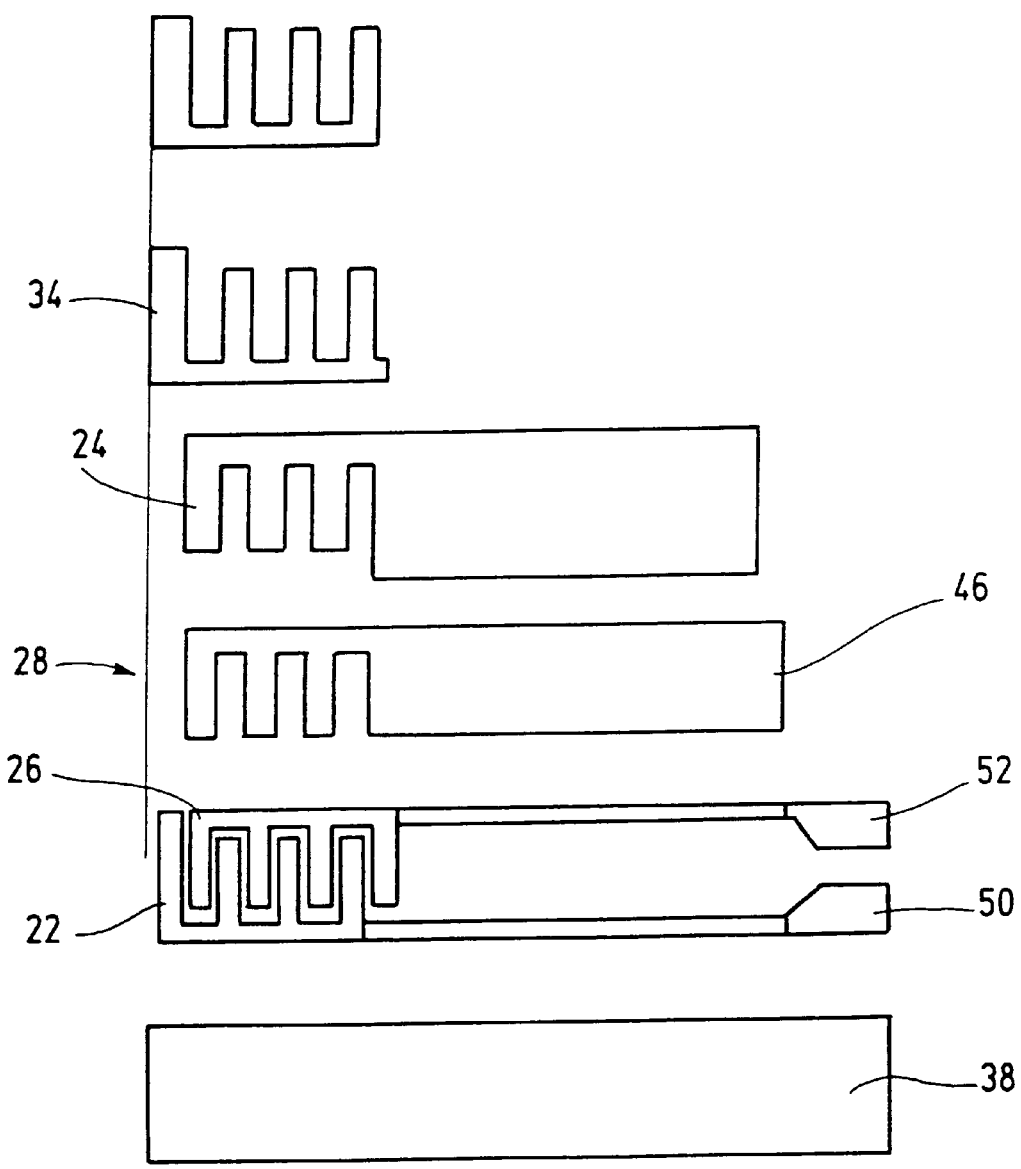
FIG. 4 shows schematic depictions of the individual functional layers of the sensing element according to FIG. 3.

FIG. 3 shows a further sectioned depiction through a sensing element 10, which although it has a modified structure is equipped with the same reference characters as in FIG. 1, which will not be explained again. Only those differences which exist will therefore be discussed. In contrast to the cross section shown in FIG. 1, FIG. 3 shows a longitudinal section through a sensing element 10. Electrodes 22 and 26 are configured here as comb electrodes lying in one plane, i.e. fingers of electrodes 22 and 26 extending from a base are alternatingly arranged next to one another, in staggered fashion, in the longitudinal extension of sensing element 10. This makes it possible to apply electrodes 22 and 26 in a single printing step. FIG. 4 shows, by analogy with FIG. 2, the individual printing steps to produce sensing device 16. Base layer 38 is first printed onto support 12 (not depicted here) with its porous adhesion layer 36, and pressed into adhesion layer 36. Electrodes 22 and 26, sacrificial layer 46, solid electrolyte 24, and protective layer 34 are then printed on. All the other process steps are analogous to the exemplary embodiment explained with reference to FIGS. 1 and 2.

Ion conduction between electrodes 22 and 26, as defined by the exemplary embodiment in FIG. 3, takes place via base layer 38, so that a signal can be picked off at connecting contacts 50 and 52. Solid electrolyte 24 arranged above the fingers of electrode 26 simultaneously constitutes reference gas conduit 20 and a cover for reference gas conduit 20 and electrode 26 with respect to an external measured gas.

What is claimed is:

1. A sensing element, for an electrochemical sensor, for determining an oxygen content of a gas, comprising:

at least one first electrode exposed to a measured gas;

at least one second electrode exposed to a reference gas;

a sensing device;

a sintered support receiving the sensing device when the sensing device is in an unsintered state; and a sintered, porous adhesion layer situated between the support and the sensing device.

2. The sensing element according to claim 1, further comprising a heating device, the heating device and the sensing device being on opposite sides of the support.

3. The sensing element according to claim 1, wherein:

the at least one first electrode and the at least one second electrode correspond to individual functional layers arranged one above the another according to a preselected layout, the functional layers are at least one of successively printed and successively pressed onto the sintered support, and the functional layers are sintered with the support.

4. The sensing element according to claim 3 wherein:

the adhesion layer that is sintered with the support is arranged onto the support.

5. The sensing element according to claim 4, wherein:

a base layer of the sensing device is pressed into the adhesion layer.

6. The sensing element according to claim 3, further comprising:

a heating device applied onto the support independently of the functional layers.

7. The sensing element according to claim 6, wherein:

the heating device is applied on a side of the support facing away from the functional layers.

8. The sensing element according to claim 3, wherein:

the heating device is sintered with the support.

* * * * *